(12) United States Patent
Roh et al.

(10) Patent No.: US 9,925,109 B2
(45) Date of Patent: Mar. 27, 2018

(54) REHABILITATION TRAINING APPARATUS

(71) Applicant: NEOFECT Co., Ltd., Yongin-si, Gyeonggi-do (KR)

(72) Inventors: Sung Jun Roh, Seoul (KR); Hyun Soo Kim, Seoul (KR); Soo Bin Lee, Seongnam-si (KR); Ho Yeong Song, Yongin-si (KR); Ho Young Ban, Yongin-si (KR); Young Geun Choi, Yongin-si (KR); Dae Hoon Jang, Guri-si (KR); Byeong Geol Park, Icheon-si (KR)

(73) Assignee: NEOFECT Co., Ltd., Yongin-si (KR)

( * ) Notice: Subject to any disclaimer, the term of this patent is extended or adjusted under 35 U.S.C. 154(b) by 0 days.

(21) Appl. No.: 15/291,070

(22) Filed: Oct. 12, 2016

(65) Prior Publication Data

US 2017/0340502 A1 Nov. 30, 2017

(30) Foreign Application Priority Data

May 27, 2016 (KR) .......................... 10-2016-0065439
Jun. 23, 2016 (KR) .......................... 10-2016-0078444

(51) Int. Cl.
*A61H 1/00* (2006.01)

(52) U.S. Cl.
CPC ....... *A61H 1/008* (2013.01); *A61H 2201/123* (2013.01); *A61H 2201/1207* (2013.01); *A61H 2201/1635* (2013.01); *A61H 2205/062* (2013.01); *A61H 2205/065* (2013.01)

(58) Field of Classification Search
CPC . A61H 1/00; A61H 1/008; A61H 1/02; A61H 1/0218; A61H 1/9274; A61H 1/0274–1/0281; A61H 2001/0207; A61H 2201/1614; A61H 2201/1616; A61H 2201/1635; A61H 2201/1638; A61H 2201/1659; A61H 2201/1666; A61H 2201/1669; A61H 2205/06–2205/065; A63B 22/0002; A63B 22/0015–22/0017; A63B 2022/002; A63B 2023/006; A63B 23/03508

See application file for complete search history.

(56) References Cited

U.S. PATENT DOCUMENTS

| | | | | |
|---|---|---|---|---|
| 4,052,039 A * | 10/1977 | Koyano | ................ | B23K 7/006 148/196 |
| 2006/0226106 A1* | 10/2006 | Zaguroli, Jr. | ............ | B66D 3/18 212/331 |
| 2015/0302777 A1* | 10/2015 | Campolo | ............. | A61H 1/0274 434/262 |

FOREIGN PATENT DOCUMENTS

KR 10-1099063 B1 12/2011

* cited by examiner

*Primary Examiner* — Rachel T Sippel
(74) *Attorney, Agent, or Firm* — Studebaker & Brackett PC

(57) ABSTRACT

Disclosed is a rehabilitation training apparatus including a pair of first tracks that are arranged in parallel at an interval, a second track that is perpendicular to the pair of first tracks and is movably connected to the pair of first tracks, a hand holder that is movably provided in the second track and on which a hand of the user is held, a holder driving unit that reciprocally moves the hand holder along the second track, and a track driving unit that reciprocally moves the second track along the pair of first tracks.

11 Claims, 6 Drawing Sheets

REHABILITATION TRAINING APPARATUS

CROSS-REFERENCE TO RELATED APPLICATIONS

A claim for priority under 35 U.S.C. § 119 is made to Korean Patent Application Nos. 10-2016-0065439 filed May 27, 2016 and 10-2016-0078444 filed Jun. 23, 2016, in the Korean Intellectual Property Office, the entire contents of which are hereby incorporated by reference.

BACKGROUND

Embodiments of the inventive concept described herein relate to a rehabilitation training apparatus, and more particularly to a rehabilitation training apparatus by which rehabilitation training of the joints of a wrist and a shoulder of the user can be performed.

In general, the joints of the human body are configured such that adjacent parts of the joints may be rotated about the joints.

Meanwhile, the aged persons or the patients with disability, whose muscular forces are weak, have difficulties in exercising their joints as compared with healthy persons, and it is substantially difficult to exercise with general sports equipment in spite of the needs of exercises.

In particular, because the patients who had surgical operations on the wrists and shoulders cannot exercise by themselves, the joints of the wrists and the shoulders may be stiff and hardened due to the weal muscles and insufficient supply of nutrients.

Accordingly, long-term rehabilitation training is necessary to prevent deformation of the joints and allow the patients to return to normal activities.

Meanwhile, most of the conventional rehabilitation apparatuses have only a function of constraining the angles of the joints of the wrists and the shoulders of the user to prevent excessive exercises.

Accordingly, studies on the rehabilitation training apparatuses configured to change the angles of the joints with actuators have been made.

Therefore, the applicant has developed a rehabilitation training apparatus by which rehabilitation training of the joints of the wrists and the shoulders can be made while a hand of the user is held.

SUMMARY

Embodiments of the inventive concept provide a rehabilitation training apparatus by which rehabilitation training may be performed by moving a hand holder in which a hand of the user is held according to characteristics of the user in various patterns and changing the angles of the joints of a wrist and a shoulder of the user.

Embodiments of the inventive concept also provide a rehabilitation training apparatus by which rehabilitation training may be performed by moving a hand holder in a desired direction by using fine muscular forces and changing the angles of the joints of a wrist and a shoulder of the user.

In accordance with an aspect of the inventive concept, there is provided a rehabilitation training apparatus including a pair of first tracks that are arranged in parallel at an interval, a second track that is perpendicular to the pair of first tracks and is movably connected to the pair of first tracks, a hand holder that is movably provided in the second track and on which a hand of the user is held, a holder driving unit that reciprocally moves the hand holder along the second track, and a track driving unit that reciprocally moves the second track along the pair of first tracks.

Here, the rehabilitation training apparatus may further include a control unit that controls driving of the holder driving unit and the track driving unit such that the hand holder is moved along a plane defined by the pair of first tracks and the second track.

The rehabilitation training apparatus may further include a pattern recognizing unit that recognizes coordinate data for a printing pattern that is provided on a printout provided on the plane defined by the pair of first tracks and the second track, and the control unit may control the driving of the holder driving unit and the track driving unit such that the hand holder is moved, based on the coordinate data for the printing pattern recognized by the pattern recognizing unit.

The rehabilitation training apparatus may further include a memory in which plane coordinate data and movement speed data for a movement pattern, in which the hand holder is to be moved, are stored, and the control unit may control the driving of the holder driving unit and the track driving unit, based on the coordinate data and the movement speed data for the movement pattern received through the memory, prior to the coordinate data for the printing pattern received from the pattern recognizing unit.

Further, the rehabilitation training apparatus may further include a communication module that receives plane coordinate data and movement speed data for a movement pattern, in which the hand holder is to be moved, from an external device, and the control unit may control the driving of the holder driving unit and the track driving unit, based on the coordinate data and the movement speed data for the movement pattern received through the communication module, prior to the coordinate data for the printing pattern received from the pattern recognizing unit.

The holder driving unit may include a guide rail for a holder that is arranged along the second track, a guide block for a holder that is connected to the hand holder to be reciprocally moved along the guide rail for a holder, a rack for a holder that has a plurality of gear teeth along a lengthwise direction of the guide rail for a holder, a pinion for a holder that is engaged with the rack for a holder to be rotated, a motor for a holder that generates a rotational force in the pinion for a holder, a clutch for a holder that engages or disengages power transmitted from the motor for a holder to the pinion for a holder, and a housing for a holder that accommodates the pinion for a holder, the motor for a holder, and the clutch for a holder and supports the hand holder.

Further, the holder driving unit may further include a power transmission unit for a holder that is provided between the motor for a holder and the pinion for a holder to transmit the power of the motor for a holder to the pinion for a holder.

The track driving unit may include a guide rail for a track that is arranged along one of the pair of first tracks, a guide block for a track, to which the second track is connected and which is reciprocally moved along the guide rail for a track, a rack for a track that has a plurality of gear teeth along a lengthwise direction of the guide rail for a track, a pinion for a track that is engaged with the rack for a track to be rotated, a motor for a track that generates a rotational force in the pinion for a track, a clutch for a track that engages or disengages power transmitted from the motor for a track to the pinion for a track, and a housing for a track that accommodates the pinion for a track, the motor for a track, and the clutch for a track and supports the guide block for a track.

The track driving unit may further include a power transmission unit for a track that is provided between the motor for a track and the pinion for a track to transmit the power of the motor for a track to the pinion for a track.

The pattern recognizing unit may be an optical recognition sensor or a photo sensor.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
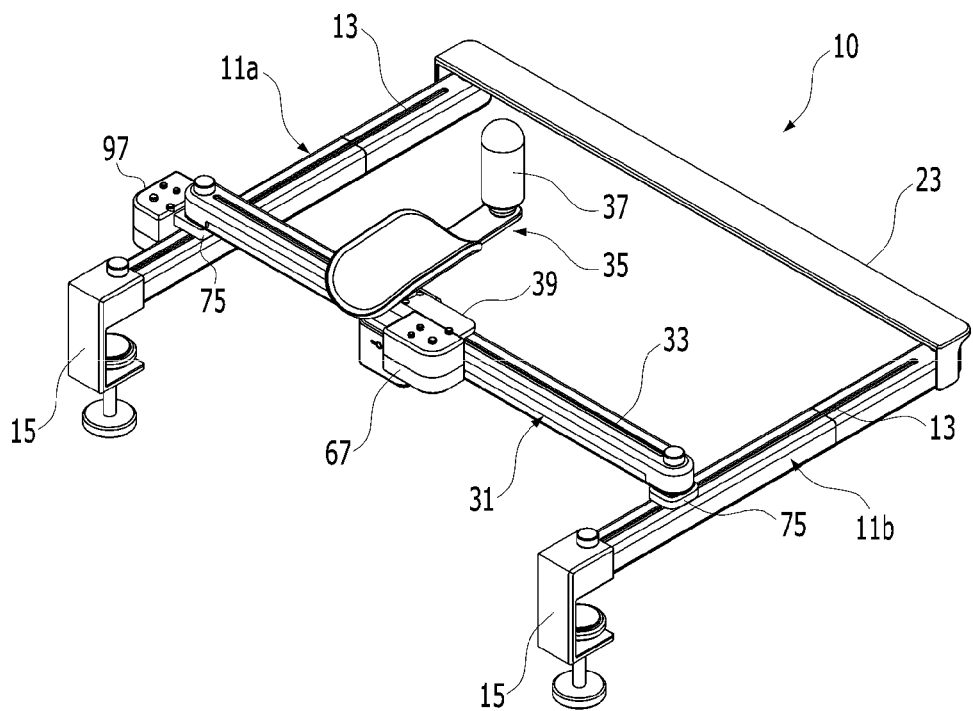
FIG. 1 is a perspective view of a rehabilitation training apparatus according to an embodiment of the inventive concept.
Figure 2:
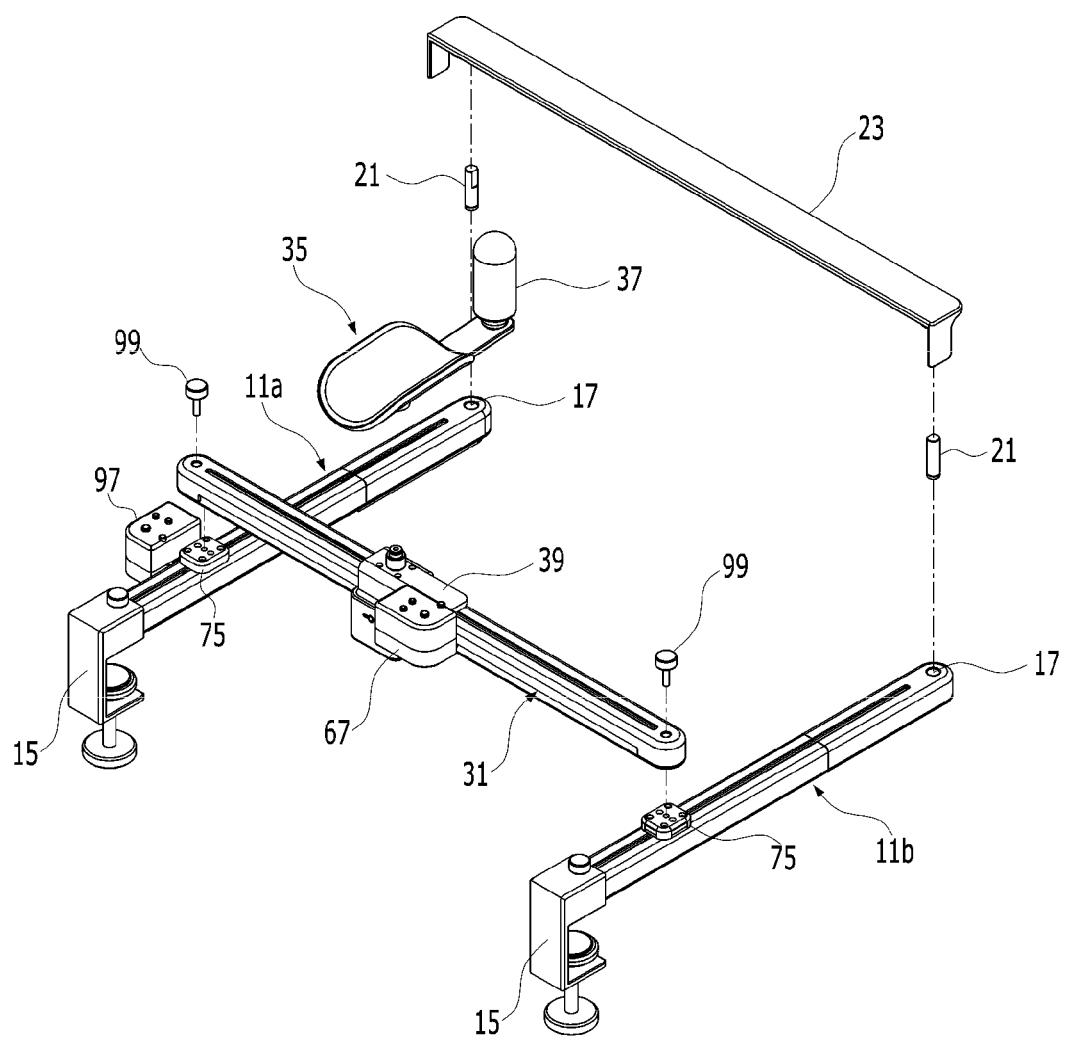
FIG. 2 is an exploded perspective view of FIG. 1.

Hereinafter, the inventive concept will be described in detail with reference to the accompanying drawings.

FIGS. 1 to 6 illustrate a rehabilitation training apparatus according to an embodiment of the inventive concept.

As illustrated in the drawings, the rehabilitation training apparatus 10 according to the embodiment of the inventive concept include a pair of first tracks 11a and 11b, a second track 31, a hand holder 35, a holder driving unit 41, and a track driving unit 71.

The pair of first tracks 11a and 11b have a bar shape having a specific length, and are arranged in parallel at a specific interval. A first track groove 13 is formed along a lengthwise direction of the first track 11a and 11b of an upper surface of each of the first tracks 11a and 11b.

A table holder 15 for seating the rehabilitation training apparatus 10 according to the embodiment of the inventive concept on a table is provided at one end of each of the pair of first tracks 11a and 11b.

A hinge pin coupling recess 17, to which a hinge pin 21 is coupled, is formed at an opposite end of each of the pair of first tracks 11a and 11b. The hinge pin 21 is rotatably coupled to the hinge pin coupling recess 17 of each of the first tracks 11a and 11b and is coupled to a connecting bracket 23. Accordingly, the connecting brackets 23 are interconnected to the pair of first tracks 11a and 11b by the hinge pins 21, respectively, and are relatively rotatable with respect to the pair of first tracks 11a and 11b such that the pair of first tracks 11a and 11b get closer to or far away from each other.

According to the rehabilitation training apparatus according to the embodiment of the inventive concept, the user may perform rehabilitation training of joints of a wrist and a shoulder after the pair of first tracks 11a and 11b and the connecting bracket 23 are simply deployed, and the user may conveniently carry the rehabilitation training apparatus and easily preserve the rehabilitation training apparatus while simply folding the pair of first tracks 11a and 11b and the connecting bracket 23 after the rehabilitation training.

The second track 31 has a bar shape having a specific length, is perpendicular to the pair of first tracks 11a and 11b, and is movably connected to the pair of first tracks 11a and 11b. A second track groove 33 is formed on an upper surface of the second track 31 along a lengthwise direction of the second track 31.

Here, the pair of first tracks 11a and 11b and the second track 31 are telescopically coupled along the lengthwise directions thereof, and for example, the tracks 11a, 11b, and 31 are retractably manufactured so that the lengths thereof may be adjusted to be extended or contracted.

The hand holder 35 is movably provided in the second track 31, and a hand of the user is held on the hand holder 35. The hand holder 35 may further include a grip 37 that is provided on one side of an upper portion thereof to be gripped by a hand. Further, the hand holder 35 further includes a support bracket 39 that is provided at a lower portion thereof to support a guide block 45 for a holder. The support bracket 39 is supported by a housing 67 for a holder arranged on one side of the second track 31, which will be described below.

Figure 3:
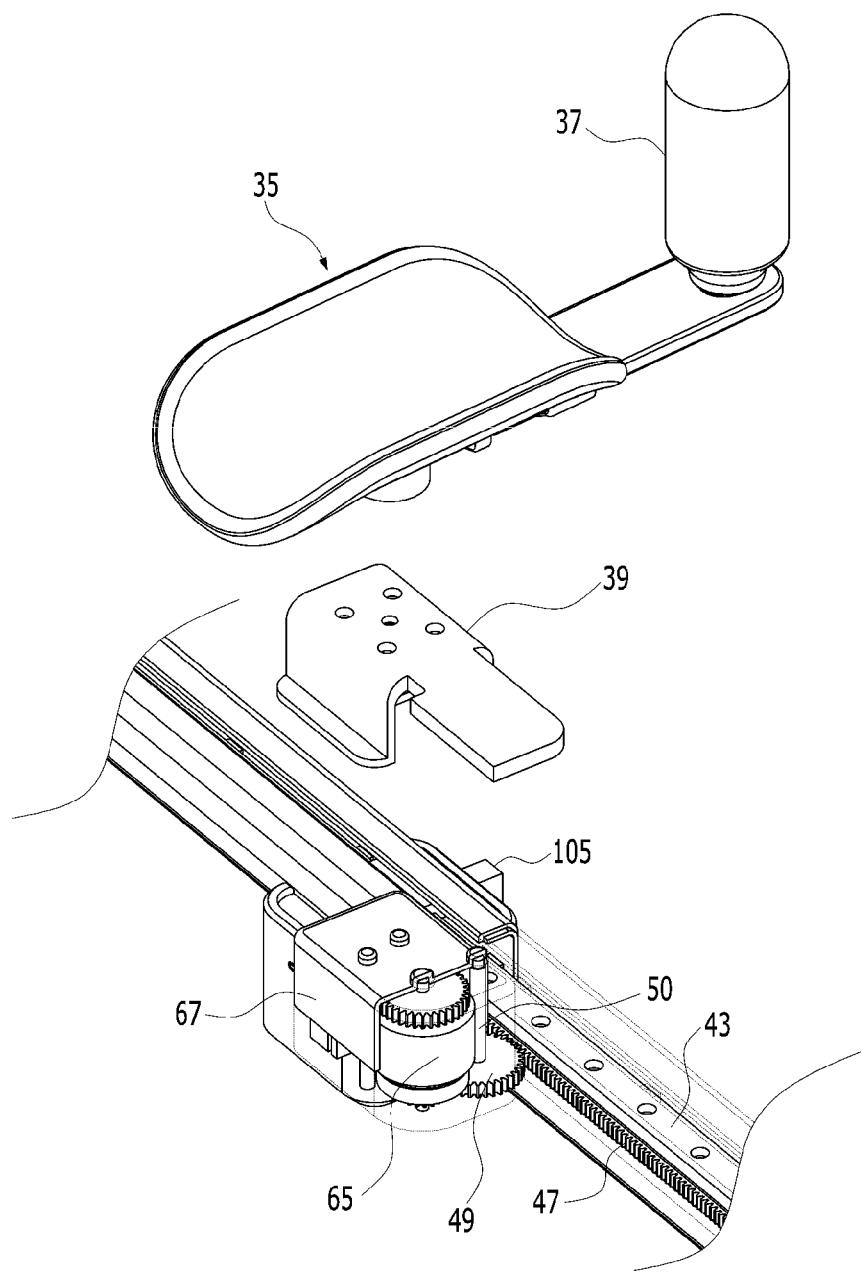
FIG. 3 is a partially enlarged perspective view of a holder driving unit of FIG. 1.
Figure 4:
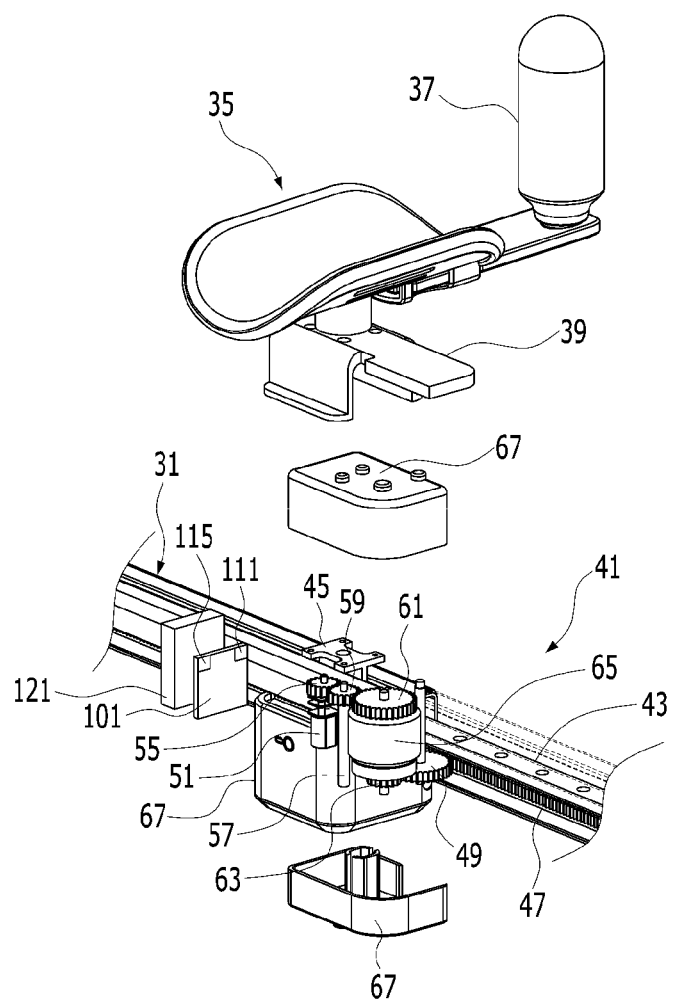
FIG. 4 is a view illustrating a power transmission system of the holder driving unit of FIG. 3.

The holder driving unit 41 reciprocates the hand holder 35 along the second track 31. As illustrated in FIGS. 3 and 4, the holder driving unit 41 includes a guide 43 for a holder that is arranged along the second track 31, a guide block 45 for a holder that is connected to the hand holder 35 to be reciprocally moved along the guide 43 for a holder, a rack 47 for a holder that has a plurality of gear teeth along a lengthwise direction of the guide 43 for a holder, a pinion 49 for a holder that is engaged with the rack 47 for a holder to be rotated, a motor 51 for a holder that generates a rotational force in the pinion 49 for a holder, a power transmission unit that is provided between the motor 51 for a holder and the pinion 49 for a holder to transmit power to the motor 51 for a holder, a clutch 65 for a holder that engages or disengages the power transmitted from the power transmission unit to the pinion 49 for a holder, and a housing 67 for a holder that supports the hand holder 35.

The guide 43 for a holder secures a movement space of the guide block 45 for a holder, and is accommodated in and coupled to the interior of the second track 31.

The guide block 45 for a holder is reciprocally coupled to the guide 43 for a holder. One side of the guide block 45 for a holder protrudes from the second track groove 33 of the second track 31 and is supported by the bottom of the support bracket 39 of the hand holder 35.

The pinion 49 for a holder is coupled to a pinion shaft 50 for a holder, and the pinion shaft 50 for a holder is rotatably supported by the housing 67 for a holder.

Meanwhile, in the embodiment, the power transmission unit for a holder includes a first gear 55 for a holder that is coupled to a shaft of the motor 51 for a holder, a second gear 59 for a holder that is engaged with the first gear 55 for a holder to be rotated and is coupled to a power transmission shaft 57 for a holder, a third gear 61 for a holder that is engaged with the second gear 59 for a holder to be rotated and is coupled to one end of the clutch 65 for a holder, and a fourth gear 63 for a holder that is coupled to an opposite end of the clutch 65 for a holder to be opposite to the third gear 61 for a holder while the clutch 65 for a holder being interposed therebetween and is engaged with the pinion 49 for a holder to be rotated.

The housing 67 for a holder has a structure that may be vertically separated, and accommodates the motor 51 for a holder, the power transmission unit for a holder, and the clutch 65 for a holder such that the motor 51 for a holder, the power transmission unit for a holder, and the clutch 65 for a holder are not exposed to the outside. Further, on one side of the housing 67 for a holder, the support bracket 39 of the hand holder 35 is supported by a coupling unit (not illustrated).

Here, although not illustrated, as another embodiment, the holder driving unit 41 does not include a power transmission unit for a holder, and the clutch 65 for a holder is interposed between the motor 51 for a holder and the pinion 49 for a holder such that power of the motor 51 for a holder may be selectively transmitted to the pinion 49 for a holder via the clutch 65 for a holder or may not be transmitted to the pinion 49 for a holder.

The track driving unit 71 reciprocally moves the second track 31 along the first tracks 11a and 11b.

Figure 5:
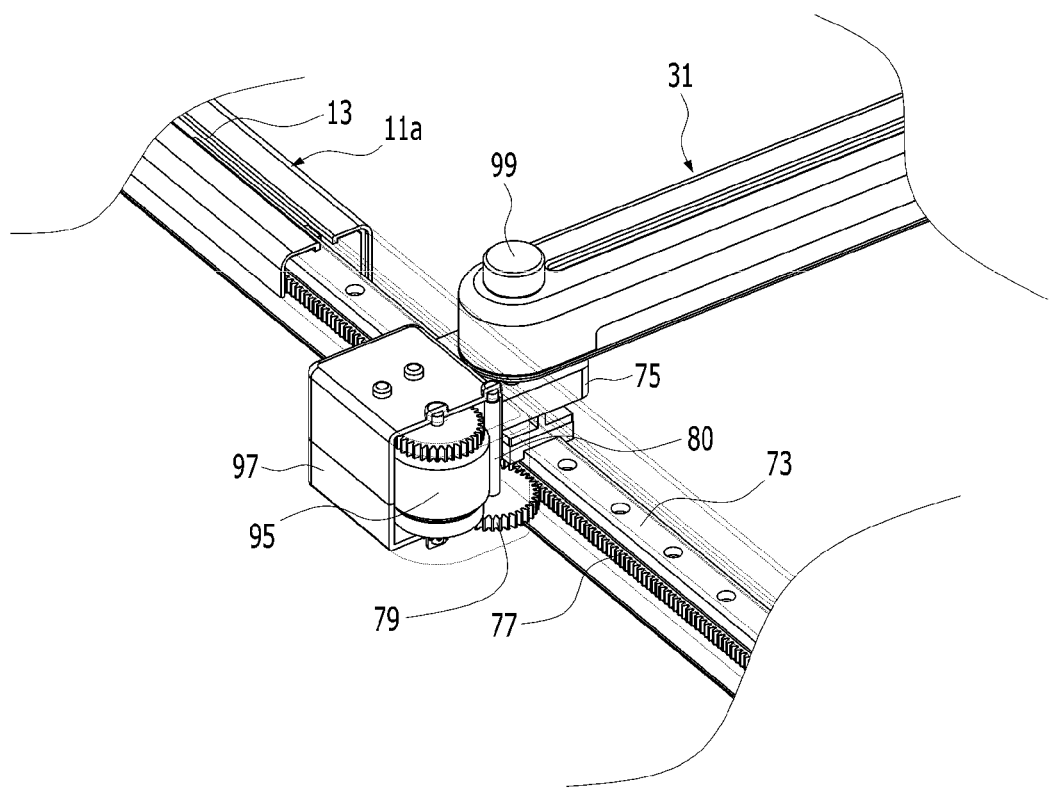
FIG. 5 is a partially enlarged perspective view of a track driving unit of FIG. 1.
Figure 6:
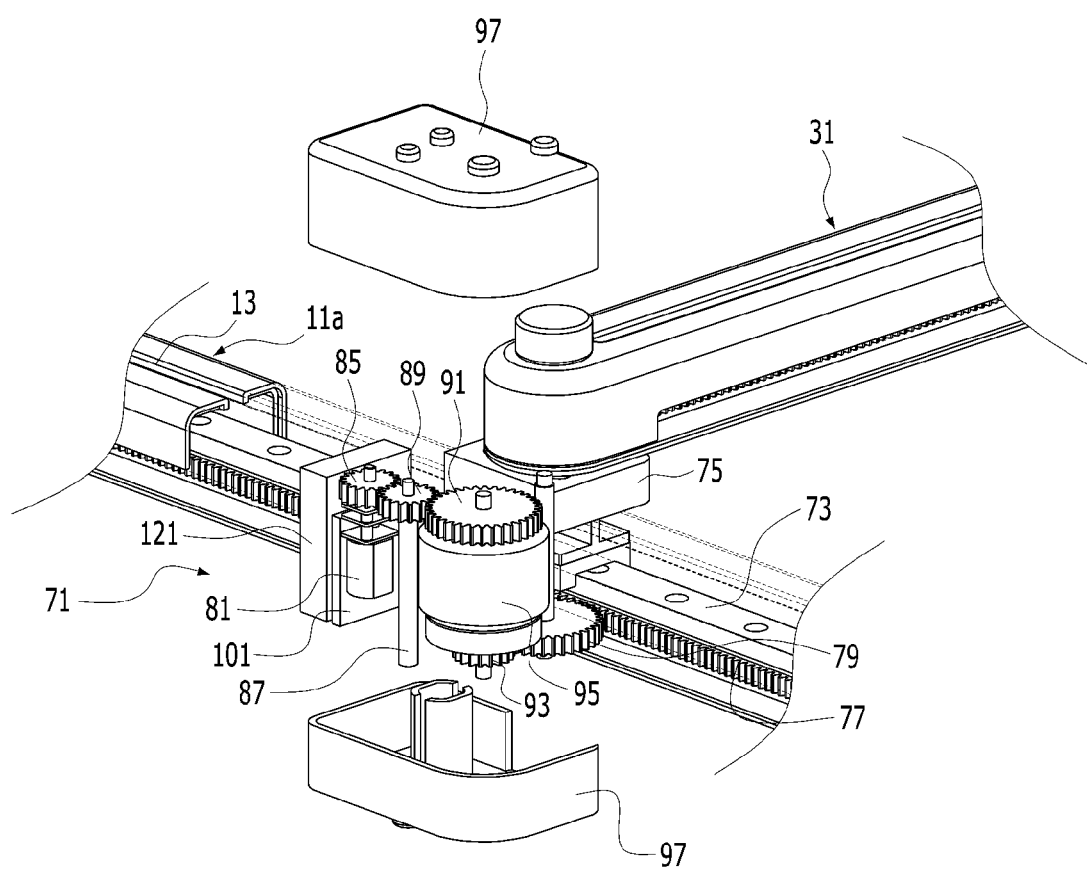
FIG. 6 is a view illustrating a power transmission system of the track driving unit of FIG. 5.

As illustrated in FIGS. 5 and 6, the track driving unit 71 includes a guide 73 for a track that is arranged along one 11a of the first tracks 11a and 11b, a guide block 75 for a track to which the second track 31 is connected and which is reciprocally moved along the guide 73 for a track, a rack 77 for a track that has a plurality of gear teeth along a lengthwise direction of the guide 73 for a track, a pinion 79 for a track that is engaged with the rack 77 for a track to be rotated, a motor 81 for a track that generates a rotational force in the pinion 79 for a track, a power transmission unit for a track that is provided between the motor 81 for a track and the pinion 79 to transmit power of the motor 81 of a track, a clutch 95 for a track that engages or disengages the power transmitted from the power transmission unit for a track to the pinion 79 for a track, and a housing 97 for a track that supports the guide block 75 for a track.

The guide 73 for a track secures a movement space of the guide block 75 for a track, and is accommodated in and coupled to the interior of the first track 11a.

The guide block 75 for a track is reciprocally coupled to the guide 73 for a track. One side of the guide block 75 for a track protrudes from the first track groove 13 of the first track 11a, and is supported by the bottom of the second track 31.

The pinion 79 for a track is coupled to a pinion shaft 80 for a track, and the pinion shaft 80 for a track is rotatably supported by the housing 97 for a track.

Meanwhile, in the embodiment, the power transmission unit for a track includes a first gear 85 for a track that is coupled to a shaft of the motor 81 for a track, a second gear 89 for a track that is engaged with the first gear 85 for a track to be rotated and is coupled to a power transmission shaft 87 for a track, a third gear 91 for a track that is engaged with the second gear 89 for a track to be rotated and is coupled to one end of the clutch 95 for a track, and a fourth gear 93 for a track that is coupled to an opposite end of the clutch 95 for a track to be opposite to the third gear 91 for a track while the clutch 95 for a track being interposed therebetween and is engaged with the pinion 79 for a track to be rotated.

The housing 97 for a track has a structure that may be vertically separated, and accommodates the motor 81 for a track, the power transmission unit for a track, and the clutch 95 for a track such that the motor 51 for a track, the power transmission unit for a track, and the clutch 65 for a track are not exposed to the outside. Further, on one side of the housing 97 for a track, the guide block 75 for a track is supported by a coupling unit (not illustrated).

Here, although not illustrated, as another embodiment, the track driving unit 71 does not include a power transmission unit for a track, and the clutch 95 for a track is interposed between the motor 81 for a track and the pinion 79 for a track such that power of the motor 81 for a track may be selectively transmitted to the pinion 79 for a track via the clutch 95 for a track or may not be transmitted to the pinion 79 for a track.

Further, the rehabilitation training apparatus 10 according to the embodiment of the inventive concept includes a control unit 101 that controls driving of the holder driving unit 41 and the track driving unit 71 such that the hand holder 35 is moved along a plane defined by the pair of first tracks 11a and 11b and the second track 31.

The control unit 101 is received in the housing 67 for a holder and controls rotational speeds and a rotational directions of the motor 51 for a holder and the motor 81 for a track to change a movement direction and a speed of the hand holder 35, based on coordinate data and movement speed data for a pattern that is set in advance along a plane defined by the pair of first tracks 11a and 11b and the second track 31. For example, if the control unit 101 controls the rotational speeds of the motor 51 for a holder and the motor 81 for a track differently, the hand holder 35 is moved linearly, in a curved manner, or while freely drawing a curve.

Here, the control unit 101 may not be received in the housing 67 for a holder but may be received in the housing 97 for a track.

Meanwhile, reference numeral 99 that has not been described denotes a coupling bolt that couples the second track 31 and the guide block 75 for a track. Further, reference numeral 121 that has not been described denotes a battery for supplying electric power to the rehabilitation training apparatus 10 according to the embodiment of the inventive concept.

According to the configuration, the rehabilitation training apparatus 10 according to the embodiment of the inventive concept may be operated in an automatic mode such that an arm of the patient is moved along a specific path by driving of the motors 51 and 81 of the holder driving unit 41 and the track driving unit 71 and may be operated in a manual mode such that an arm of the patient is moved along a specific path by a force of the user.

First, a case in which the rehabilitation training apparatus 10 is operated in a manual mode will be described below.

After a hand and an arm of the user is held on the hand holder 35, the angle of the joints of a wrist and a shoulder of the user may be changed for rehabilitation training, by applying a force to freely move the hand holder 35 along arrangement directions of the first tracks 11a and 11b and an arrangement direction of the second track 31, for example, moving the hand holder 35 in a desired direction by using a fine muscular force of the user. Then, the clutch 65 for a holder of the holder driving unit 41 disengages transmission of power so that the power of the motor 51 for a holder is not transmitted to the pinion 49 for a holder. At the same time, the clutch 95 for a track of the track driving unit 71 disengages transmission of power so that the power of the motor 81 for a track is not transmitted to the pinion 79 for a track.

Next, a case in which the rehabilitation training apparatus 10 is operated in an automatic mode will be described below.

The control unit 101 drives the holder driving unit 41 and the track driving unit 71 such that the hand holder 35 is moved along the plane defined by the pair of first tracks 11a and 11b and the second track 31.

That is, if the clutch 65 for a holder is switched to a power transmission state by a control signal of the control unit 101 and the motor 51 for a holder is forwardly rotated by applying an electric voltage to the motor 51 for a holder such that the power of the motor 51 for a holder is transmitted to the pinion 49 for a holder, the power of the motor 51 for a holder is transmitted to the first gear 55 for a holder, the second gear 59 for a holder, the third gear 61 for a holder, the fourth gear 63 for a holder, and the pinion 49 for a holder. Accordingly, the pinion 49 for a holder is reciprocally moved along the rack 47 for a holder and the housing 67 for a holder is reciprocally moved along the second track 31 at the same time, and the hand holder 35 connected to the housing 67 for a holder and the guide block 45 for a holder is guided by the guide 43 for a holder and is reciprocally moved along the second track 31.

At the same time, if the clutch 95 for a track is switched to a power transmission state by a control signal of the control unit 101 and the motor 81 for a track is forwardly rotated by applying an electric voltage to the motor 81 for a track such that the power of the motor 81 for a track is transmitted to the pinion 79 for a track, the power of the motor 81 for a track is transmitted to the first gear 85 for a track, the second gear 89 for a track, the third gear 91 for a track, the clutch 95 for a track, the fourth gear 93 for a track, and the pinion 79 for a track. Accordingly, the pinion 79 for a track is linearly reciprocally moved along the rack 77 for a track and the housing 97 for a track is reciprocally moved along one 11*a* of the first tracks 11*a* and 11*b* at the same time, and the guide block 45 for a track connected to the housing 97 for a track is guided by the guide 73 for a track and is reciprocally moved along the first track 11*a*. Accordingly, the second track 31 supported by the guide block 75 for a track is also reciprocally moved along the first tracks 11*a* and 11*b*.

Accordingly, the hand of the user held by the hand holder 35 is moved by a control signal of the control unit 101 while forming various patterns along the plane defined by the pair of first tracks 11*a* and 11*b* and the second track 31, on the plane defined by the pair of first tracks 11*a* and 11*b* and the second track 31, so that rehabilitation training may be performed while the angles of the joints of a wrist and a shoulder of the user is changed.

Here, the control unit 101 may switch the clutch 65 for a holder to a power transmission state such that the power of the motor 51 for a holder is transmitted to the pinion 49 for a holder, switch the clutch 95 for a track to a power interruption state such that the power of the motor 81 for a track is not transmitted to the pinion 79 for a track, and reciprocally move the hand holder 35 only in the direction of the second track, thereby allowing the user to perform rehabilitation training for the joints of the wrists and a shoulder of the user.

Meanwhile, the rehabilitation training apparatus 10 according to the embodiment of the inventive concept may further include a pattern recognizing unit 105 that is provided in the hand holder 35 to recognize coordinate data for a printing pattern printed in a printout provided on the plane defined by the pair of first tracks 11*a* and 11*b* and the second track 31. The pattern recognizing unit 105 may be an optical recognition sensor or a photo sensor. Although it is illustrated in the embodiment that the pattern recognizing unit 105 is provided in the housing 67 for a holder, the inventive concept is not limited thereto and the pattern recognizing unit 105 may be provided in the second track 31.

In this way, when the pattern recognizing unit 105 is provided, the control unit 101 may control driving of the holder driving unit 41 and the track driving unit 71 such that the hand holder 35 is moved, based on the coordinate data for the printing pattern recognized by the pattern recognizing unit 105.

Further, the rehabilitation training unit 10 according to the embodiment of the inventive concept may further include a memory that is provided in the housing 67 for a hand holder and in which plane coordinate data and movement speed data for the movement pattern, in which the hand holder 35 is to be moved, are stored.

In this way, when the memory 111 is provided, the control unit 101 may control the driving of the holder driving unit 41 and the track driving unit 71, based on the coordinate data and the movement speed data for the movement pattern received through the memory 111, prior to the coordinate data for the printing pattern received from the pattern recognizing unit 105.

That is, the memory 111 provides the plane coordinate data and the movement speed data for the movement pattern, in which the hand holder 35 stored in the memory 111 is to be moved, to the control unit 101.

The control unit 101 controls movement of the hand holder 35, by controlling the rotational speeds and the directions of the motor 51 for a holder and the motor 81 for a track, based on the coordinate data and the movement speed data for the movement pattern provided through the memory 111.

In this way, as the memory 111 is provided, rehabilitation training may be performed by selectively receiving a movement pattern through the memory 111 according to the characteristics of the user and changing the angles of the joints in a preset direction based on the coordinate data and the movement speed data for the movement pattern stored in the memory 111 while a hand of the user is held in the hand holder 35.

Further, the rehabilitation training unit 10 according to the embodiment of the inventive concept may further include a communication module that is provided in the housing 67 for a holder to receive plane coordinate data and movement speed data for the movement pattern, in which the hand holder 35 is to be moved, from an external device.

In this way, when the communication module 115 is provided, the control unit 101 may control the driving of the holder driving unit 41 and the track driving unit 71, based on the coordinate data and the movement speed data for the movement pattern received through the communication module 115, prior to the coordinate data for the printing pattern received from the pattern recognizing unit 105.

That is, the control unit 101 controls movement of the hand holder 35, by controlling the rotational speeds and the directions of the motor 51 for a holder and the motor 81 for a track, based on the coordinate data and the movement speed data for the movement pattern provided through the communication module 115.

In this way, as the communication module 115 is provided, rehabilitation training may be performed by transmitting a control signal for the movement pattern according to the characteristics of the user to the control unit 101 through the communication module 115 and changing the angles of the joints in various directions based on the coordinate data and the movement speed data for the movement pattern received through the communication module while a hand of the user is held in the hand holder 35.

Here, when the communication module 115 is provided, the control unit 101 may control the driving of the holder driving unit 41 and the track driving unit 71 according to the coordinate data and the movement speed data for the movement pattern received through the communication module 115, prior to the coordinate data and the movement data for the printing pattern received from the pattern recognizing unit 105 or the coordinate data and the movement speed data for the movement pattern provided through the memory 111.

In this way, according to the inventive concept, rehabilitation training may be performed by movably arranging the second track in the pair of first tracks arranged in parallel at an interval, reciprocating the hand holder in which a hand of the user is held along the second track and reciprocating the second track along the pair of first tracks at the same time to move the hand holder according to the characteristics of the user I various patterns, and changing the angles of the joints of a wrist and a shoulder of the user.

According to the inventive concept, rehabilitation training may be performed by moving a hand holder in which a hand of the user is held according to characteristics of the user in various patterns and changing the angles of the joints of a wrist and a shoulder of the user. Further, rehabilitation training may be performed by moving a hand holder in a desired direction by using fine muscular forces and changing the angles of the joints of a wrist and a shoulder of the user.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A rehabilitation training apparatus, comprising:
   a pair of first tracks that are arranged in parallel at an interval;
   a second track that is perpendicular to the pair of first tracks and is movably connected to the pair of first tracks;
   a hand holder that is movably provided in the second track and on which a hand of a user is adapted to be held;
   a holder driving unit that reciprocally moves the hand holder along the second track; and
   a track driving unit that reciprocally moves the second track along the pair of first tracks and comprises a track motor,
   wherein the holder driving unit comprises:
      a holder rack that has a plurality of gear teeth along a lengthwise direction of the second track;
      a holder pinion that is engaged with the gear teeth of the holder rack, and configured to be rotated; and
      a holder motor configured to move the hand of the user along a predetermined path, by generating a rotational force and transmitting the generated force to the holder pinion,
   wherein the holder driving unit includes a control unit that controls both of the track motor and the holder motor, and
   wherein the control unit of the holder driving unit controls the hand holder to move in a curved manner, by controlling the track motor and the holder motor to have different rotation speeds from each other.

2. The rehabilitation training apparatus of claim 1, wherein the control unit controls driving of the holder driving unit and the track driving unit such that the hand holder is moved along a plane defined by the pair of first tracks and the second track.

3. The rehabilitation training apparatus of claim 2, further comprising:
   a pattern recognizing unit that recognizes coordinate data for a printing pattern to be provided on the plane defined by the pair of first tracks and the second track,
   wherein the control unit controls the driving of the holder driving unit and the track driving unit such that the hand holder is moved, based on the coordinate data for the printing pattern recognized by the pattern recognizing unit.

4. The rehabilitation training apparatus of claim 3, further comprising:
   a memory in which plane coordinate data and movement speed data for a movement pattern, in which the hand holder is to be moved, are stored,
   wherein the control unit controls the driving of the holder driving unit and the track driving unit, based on the coordinate data and the movement speed data for the movement pattern received through the memory, prior to the coordinate data for the printing pattern received from the pattern recognizing unit.

5. The rehabilitation training apparatus of claim 3, further comprising:
   a communication module that receives plane coordinate data and movement speed data for a movement pattern, in which the hand holder is to be moved, from an external device,
   wherein the control unit controls the driving of the holder driving unit and the track driving unit, based on the coordinate data and the movement speed data for the movement pattern received through the communication module, prior to the coordinate data for the printing pattern received from the pattern recognizing unit.

6. The rehabilitation training apparatus of claim 3, wherein the pattern recognizing unit comprises at least one of an optical recognition sensor and a photo sensor.

7. The rehabilitation training apparatus of claim 1, wherein the holder driving unit comprises:
   a holder guide rail that is arranged along the second track, wherein the plurality of gear teeth of the holder rack is disposed along a lengthwise direction of the holder guide rail;
   a holder guide block that is connected to the hand holder to be reciprocally moved along the holder guide rail;
   a holder clutch that engages or disengages power transmitted from the holder motor to the holder pinion; and
   a holder housing that accommodates the holder pinion, the holder motor, and the holder clutch and supports the hand holder.

8. The rehabilitation training apparatus of claim 7, wherein the holder driving unit further comprises:
   a holder power transmission unit that is provided between the holder motor and the holder pinion to transmit the power of the holder motor to the holder pinion.

9. The rehabilitation training apparatus of claim 1, wherein the track driving unit comprises:
   a track guide rail that is arranged along one of the pair of first tracks;
   a track guide block, to which the second track is connected and which is reciprocally moved along the track guide rail;
   a track rack that has a plurality of gear teeth along a lengthwise direction of the track guide rail;
   a track pinion that is engaged with the track rack to be rotated;
   the track motor that generates a rotational force in the track pinion;
   a track clutch that engages or disengages power transmitted from the track motor to the track pinion; and
   a track housing that accommodates the track pinion, the track motor, and the track clutch and supports the track guide block.

10. The rehabilitation training apparatus of claim 9, wherein the track driving unit further comprises:

a track power transmission unit that is provided between the track motor and the track pinion to transmit the power of the track motor to the track pinion.

11. A rehabilitation training apparatus, comprising:
a pair of first tracks that are arranged in parallel at an interval;
a second track that is perpendicular to the pair of first tracks and is movably connected to the pair of first tracks;
a hand holder that is movably provided in the second track and on which a hand of a user is adapted to be held;
a holder driving unit that reciprocally moves the hand holder along the second track; and
a track driving unit that reciprocally moves the second track along the pair of first tracks,
wherein the holder driving unit comprises:
   a holder rack that has a plurality of gear teeth along a lengthwise direction of the second track;
   a holder pinion that is engaged with the gear teeth of the holder rack, and configured to be rotated; and
   a holder motor configured to move the hand of the user along an X-axis of a predetermined path, by generating a rotational force and transmitting the generated force to the holder pinion, and
wherein the track driving unit comprises:
   a track rack that has a plurality of gear teeth along a lengthwise direction of one of the pair of first tracks;
   a track pinion that is engaged with the track rack, and configured to be rotated; and
   a track motor configured to move the hand of the user along a Y-axis of the predetermined path, by generating a rotational force and transmitting the generated force to the track pinion,
wherein the track driving unit includes a control unit that controls both of the track motor and the holder motor, and
wherein the control unit of the track driving unit controls the hand holder to move in a curved manner, by controlling the track motor and the holder motor to have different rotation speeds from each other.

* * * * *